US007732467B2

(12) United States Patent
Mullan et al.

(10) Patent No.: US 7,732,467 B2
(45) Date of Patent: Jun. 8, 2010

(54) METHOD FOR REDUCING AMYLOID DEPOSITION, AMYLOID NEUROTOXICITY AND MICROGLIOSIS

(75) Inventors: Michael J. Mullan, Bradenton, FL (US); Daniel Paris, Bradenton, FL (US)

(73) Assignee: Alzheimer's Institute of America, Inc., Kansas City, KS (US)

( * ) Notice: Subject to any disclaimer, the term of this patent is extended or adjusted under 35 U.S.C. 154(b) by 1502 days.

(21) Appl. No.: 10/847,630

(22) Filed: May 17, 2004

(65) Prior Publication Data

US 2005/0009885 A1 Jan. 13, 2005

Related U.S. Application Data

(60) Provisional application No. 60/470,694, filed on May 15, 2003.

(51) Int. Cl.
*A61K 31/44* (2006.01)
(52) U.S. Cl. .................................................. 514/355
(58) Field of Classification Search ................. 514/355
See application file for complete search history.

(56) References Cited

U.S. PATENT DOCUMENTS

| | | | |
|---|---|---|---|
| 4,338,322 A | 7/1982 | Sato et al. |
| 4,654,206 A | 3/1987 | Okuda et al. |
| 4,820,720 A | 4/1989 | Sanders et al. |
| 4,859,688 A | 8/1989 | Yamaguchi et al. |
| 4,902,514 A | 2/1990 | Barclay et al. |
| 4,992,445 A | 2/1991 | Lawter et al. |
| 5,001,139 A | 3/1991 | Lawter et al. |
| 5,045,553 A | 9/1991 | Ueda et al. |
| 5,053,419 A | 10/1991 | Lipton et al. |
| 5,114,946 A | 5/1992 | Lawter et al. |
| 5,160,734 A | 11/1992 | Ganesan et al. |
| 5,340,591 A | 8/1994 | Nakano et al. |
| 6,271,259 B1 | 8/2001 | Kakuda et al. |
| 6,294,544 B1 | 9/2001 | Araie et al. |
| 6,420,405 B2 | 7/2002 | Inada et al. |
| 6,818,200 B2 | 11/2004 | Foster et al. |
| 2001/0011098 A1 | 8/2001 | Inada et al. |
| 2002/0042405 A1 | 4/2002 | Schuh |
| 2002/0094995 A1 | 7/2002 | Foster et al. |
| 2003/0013699 A1 | 1/2003 | Davis et al. |
| 2003/0044845 A1 | 3/2003 | Jenkins et al. |
| 2003/0055027 A1 | 3/2003 | Schun |
| 2003/0139801 A1 | 7/2003 | Sirhan et al. |
| 2004/0063730 A1 | 4/2004 | Eggenweiler et al. |
| 2004/0072846 A1 | 4/2004 | Eggenweiler et al. |
| 2004/0101517 A1 | 5/2004 | Bolton et al. |
| 2005/0031651 A1 | 2/2005 | Gervais et al. |

FOREIGN PATENT DOCUMENTS

DE    4141646 A1    6/1993

| | | |
|---|---|---|
| DE | 42 29 805 A1 | 3/1994 |
| EP | 0 294 601 A2 | 12/1988 |
| EP | 0 301 133 A2 | 2/1989 |
| EP | 0 317 780 A1 | 5/1989 |
| EP | 0 628 313 A1 | 12/1994 |
| EP | 1 260 232 A1 | 11/2002 |
| EP | 1 285 655 A1 | 2/2003 |
| JP | 61129140 A2 | 6/1986 |
| JP | 03117658 A2 | 5/1990 |
| JP | 03099061 A2 | 4/1991 |
| JP | 03123730 A2 | 5/1991 |
| JP | 05139974 A2 | 6/1993 |
| JP | 2001335483 A2 | 12/2001 |
| JP | 2002087959 A2 | 3/2002 |
| JP | 2002097140 A2 | 4/2002 |
| JP | 2003146878 A2 | 5/2003 |
| JP | 03470096 B2 | 11/2003 |
| JP | 2004002460 A2 | 1/2004 |
| KR | 0222306 B1 | 10/1999 |
| WO | WO 92/03137 | 3/1992 |
| WO | WO 93/05770 | 1/1993 |

(Continued)

OTHER PUBLICATIONS

Maxwelli et al., "Calcium-channel blockers and cognitive function in ederly people: results from the Canadian Study of Health and Aging." *CMAJ* 161(5):501-506, 1999.

Meredith and Elliot, "Dihydropyridine calcium channel blockers: basic pharmacological similarities but fundamental therapeutic differences." *J Hypertens* 22:1641-1648, 2004.

Yamada et al., "Alterations in calcium antagonist receptors and calcium content in senescent brain and attenuation by nimodipine and nicardipine." *JRET* 277:721-727, 1996.

(Continued)

*Primary Examiner*—Jennifer M Kim
(74) *Attorney, Agent, or Firm*—Bryan Cave LLP

(57) ABSTRACT

The present invention provides methods for reducing β-amyloid deposition, β-amyloid neurotoxicity and microgliosis in animals or humans afflicted with a cerebral amyloidogenic disease, such as Alzheimer's disease (AD), by administering therapeutically effective amounts of the dihydropyridine calcium channel antagonist, nilvadipine. The present invention also provides methods for diagnosing cerebral amyloidogenic diseases in animals or humans. Further provided are methods for reducing the risk of β-amyloid deposition, β-amyloid neurotoxicity and microgliosis in animals or humans suffering from traumatic brain injury by administering nilvadipine immediately after the traumatic brain injury and continuing treatment for a prescribed period of time thereafter. Finally, methods are provided for treating transplantable neuronal stem cells by administering nilvadipine to the neuronal stem cells prior to transplantation in the central nervous system of an animal or human afflicted with a cerebral amyloidogenic disease, such as AD.

12 Claims, 7 Drawing Sheets

FOREIGN PATENT DOCUMENTS

| WO | WO 99/63992 | 12/1999 |
|---|---|---|
| WO | WO 99/64045 | 12/1999 |
| WO | WO 00/02543 | 1/2000 |
| WO | WO 02/060461 A | 8/2002 |
| WO | WO 02/096415 A2 | 12/2002 |
| WO | WO 03/097045 A1 | 11/2003 |
| WO | WO 03/097067 A1 | 11/2003 |
| WO | WO 03/097098 A1 | 11/2003 |
| WO | WO 2004/034963 A2 | 4/2004 |
| WO | WO 2004/058258 A | 7/2004 |

OTHER PUBLICATIONS

Prof. Dr. med. Michael Strupp, Recent treatment studies in Alzheimer's disease, MS, cluster headache, focal cortical dysplasia and ALS, J Neurol 251:1546-1548, (2004).

McGreer, Patrick L. and Edith G. McGreer, "Inflammation of the brain in Alzheimer's disease: implications for therapy," Journal of Leukocyte Biology, Apr. 1999, vol. 65: 409-415.

Nilsson, Lars N. G., et al., "Alpha-1-Antichymotrypsin Promotes Beta-Sheet Amyloid Plaque Deposition in a Transgenic Mouse Model of Alzheimer's Disease," The Journal of Neuroscience, Mar. 2001, 21(5):1444-1451.

The Effect of Chronic Administration of Nilvadipine on Microglial Activation in TgAppsw Mice in Three Regions of the Brain Using a CD45 Immunostaining Technique that Determines the Number of CD45+Microglia The Effect of Nilvadipine on Microglial Activation in N9 Murine Microglial Cells In Vitro Activated with Lipopolysaccharide (LPS) for 24 Hours. Microglial Activation is Determined by TNF-Alpha Production (pg/ml) Measured by ELISA.

The Effect of Nilvadipine Adminstration on Ab Neurotoxicity Using HPNC Cells Treated for Three Days with 30mM of Pre-aggregated Ab1-40 (AgAb). Neurotoxicity is Assessed by Measuring the Amount of Lactic Dehydrogenase (LDH) Released from Cells.

The Effect of Nilvadipine on APP Processing using Human Glioblastoma Cells Transfected with APPsw. Cells were Treated with 50 nM and 250 nM Nilvadipine for (A) 24 Hours and (B) 48 Hours. Production of Ab1-40 in the Culture Medium was Measured by ELISA.

The Effect of Nilvadipine on APP Processing using Human Glioblastoma Cells Transfected with APPsw. Cells were Treated with 50 nM and 250 nM Nilvadipine for (A) 24 Hours and (B) 48 Hours. Production of Ab1-40 in the Culture Medium was Measured by ELISA.

Effect of Nilvadipine on plasma Aβ levels in 2 year-old Tg PS/APPsw mice. Animals were treated intraperitoneally every day for 3 and half weeks with nilvadipine (1.5 mg/Kg of body weight).

METHOD FOR REDUCING AMYLOID DEPOSITION, AMYLOID NEUROTOXICITY AND MICROGLIOSIS

The present invention claims priority to U.S. Provisional Application Ser. No. 60/470,694, filed May 15, 2003, which is herein incorporated by reference.

BACKGROUND OF THE INVENTION

1. Field of the Invention

The present invention relates to a method for treating the pathophysiological effects of cerebral amyloidogenic diseases, such as Alzheimer's disease. More specifically, the method involves administering a specific dihydropyridine antagonist calcium channel blocker, nilvadipine, which opposes such pathophysiological effects in the brain of animals or humans afflicted with diseases associated with cerebral amyloidosis, such as Alzheimer's disease.

2. Description of Related Art

Alzheimer's disease (AD) is the most common neurodegenerative disorder of aging, afflicting approximately 1% of the population over the age of 65. Characteristic features of the disease include the progressive accumulation of intracellular neurofibrillary tangles, extracellular parenchymal senile plaques, and cerebrovascular deposits in the brain. The principal component of senile plaques and cerebrovascular deposits is the 39-43 amino acid β-amyloid peptide (Aβ), which is proteolytically derived from amyloid precursor protein (APP), a transmembrane glycoprotein.

APP is a single-transmembrane protein with a 590-680 amino acid extracellular amino terminal domain and an approximately 55 amino acid cytoplasmic tail. Messenger RNA from the APP gene on chromosome 21 undergoes alternative splicing to yield eight possible isoforms, three of which (the 695, 751 and 770 amino acid isoforms) predominate in the brain. APP undergoes proteolytic processing via three enzymatic activities, termed α-, β- and γ-secretase. Alpha-secretase cleaves APP at amino acid 17 of the Aβ domain, thus releasing the large soluble amino-terminal fragment α-APP for secretion. Because α-secretase cleaves within the Aβ domain, this cleavage precludes Aβ formation. Alternatively, APP can be cleaved by β-secretase to define the amino terminus of Aβ and to generate the soluble amino-terminal fragment β-APP. Subsequent cleavage of the intracellular carboxy-terminal domain of APP by γ-secretase results in the generation of multiple peptides, the two most common being 40-amino acid Aβ (Aβ40) and 42-amino acid Aβ (Aβ42). Aβ40 comprises 90-95% of the secreted Aβ and is the predominant species recovered from cerebrospinal fluid (Seubert et al., *Nature*, 359:325-7, 1992). In contrast, less than 10% of secreted Aβ is Aβ42. Despite the relative paucity of Aβ42 production, Aβ42 is the predominant species found in plaques and is deposited initially, perhaps due to its ability to form insoluble amyloid aggregates more rapidly than Aβ40 (Jarrett et al., *Biochemistry*, 32:4693-7, 1993). The abnormal accumulation of Aβ in the brain is believed due to either over-expression or altered processing of APP.

Aβ peptides are thus believed to play a critical role in the pathobiology of AD, as all the mutations associated with the familial form of AD result in altered processing of these peptides from APP. Indeed, deposits of insoluble, or aggregated, fibrils of Aβ in the brain are a prominent neuropathological feature of all forms of AD, regardless of the genetic predisposition of the subject.

Concomitant with Aβ deposition, there exists robust activation of inflammatory pathways in AD brain, including production of pro-inflammatory cytokines and acute-phase reactants in and around Aβ deposits (McGeer et al., *J Leukocyte Biol.*, 65:409-15, 1999). Activation of the brain's resident innate immune cells, the microglia, is thought to be intimately involved in this inflammatory cascade. It has been demonstrated that reactive microglia produce pro-inflammatory cytokines, such as inflammatory proteins and acute phase reactants, such as alpha-1-antichymotrypsin, transforming growth factor β, apolipoprotein E and complement factors, all of which have been shown to be localized to Aβ plaques and to promote Aβ plaque "condensation" or maturation (Nilsson et al., *J. Neurosci.* 21:1444-5, 2001), and which at high levels promote neurodegeneration. Epidemiological studies have shown that patients using non-steroidal anti-inflammatory drugs (NSAIDS) have as much as a 50% reduced risk for AD (Rogers et al., *Neurobiol. Aging* 17:681-6, 1996), and post-mortem evaluation of AD patients who underwent NSAID treatment has demonstrated that risk reduction is associated with diminished numbers of activated microglia (Mackenzie et al., *Neurology* 50:986-90, 1998). Further, when Tg $APP_{sw}$ mice, a mouse model for Alzheimer's disease, are given an NSAID (ibuprofen), these animals show reduction in Aβ deposits, astrocytosis, and dystrophic neurites correlating with decreased microglial activation (Lim et al., *J. Neurosci.* 20:5709-14, 2000).

Products of the inflammatory process in the AD brain therefore may exacerbate AD pathology. Furthermore, there is evidence that activated microglia in AD brain, instead of clearing Aβ, are pathogenic by promoting Aβ fibrillogenesis and consequent deposition as senile plaques (Wegiel et al., *Acta Neuropathol.* (Berl.) 100:356-64, 2000).

It also has been suggested that AD pathogenesis is due to the neurotoxic properties of Aβ. The cytotoxicity of Aβ was first established in primary cell cultures from rodent brains and also in human cell cultures. The work of Mattson et al. (*J. Neurosci.*, 12:376-389, 1992) indicates that Aβ, in the presence of the excitatory neurotransmitter glutamate, causes an immediate pathological increase in intracellular calcium, which is believed to be very toxic to the cell through its greatly increased second messenger activities.

Thus, there exists a need for a prophylaxis for the inexorable progression of brain degeneration that is a hallmark of AD, wherein the prophylaxis addresses the Aβ deposition, Aβ neurotoxicity, microglial-activated inflammation, and altered or overexpression of APP that is seen in AD patients.

SUMMARY OF THE INVENTION

In order to meet this need, the present invention provides for the first time methods for reducing β-amyloid deposition, β-amyloid neurotoxicity and microgliosis in animals or humans afflicted with a cerebral amyloidogenic disease, such as Alzheimer's disease (AD), by administering therapeutically effective amounts of the dihydropyridine calcium channel antagonist, nilvadipine.

The present invention also provides methods for diagnosing cerebral amyloidogenic diseases, such has AD, in an animal or human, or determining if the animal or human is at risk for developing cerebral amyloidogenic disease, by taking a first measurement of the plasma concentration of β-amyloid in the peripheral circulation of the animal or human; administering a therapeutically effective amount of nilvadipine in unit dosage form to the animal or human; taking a second measurement of the plasma concentration of β-amyloid in the peripheral circulation of the animal or human at a later time; and calculating the difference between the first measurement and the second measurement of the plasma concentration of Aβ. An increase in the plasma concentration of β-amyloid in the second measurement compared to the first measurement indicates a risk of developing and/or a possible diagnosis of a cerebral amyloidogenic disease in the animal or human.

The present invention further provides methods for reducing the risk of β-amyloid deposition, β-amyloid neurotoxicity and microgliosis in animals or humans suffering from traumatic brain injury by administering to the animal or human a therapeutically effective amount of nilvadipine in unit dosage form immediately after the head injury and continuing nilvadipine treatment for a prescribed period of time thereafter.

The present invention also provides methods for treating transplantable neuronal stem cells, comprising administering a therapeutically effective amount of nilvadipine to the neuronal stem cells prior to transplantation of the stem cells in the central nervous system of an animal or human afflicted with a cerebral amyloidogenic disease, such as AD.

DESCRIPTION OF THE PREFERRED EMBODIMENTS

Figure 1:
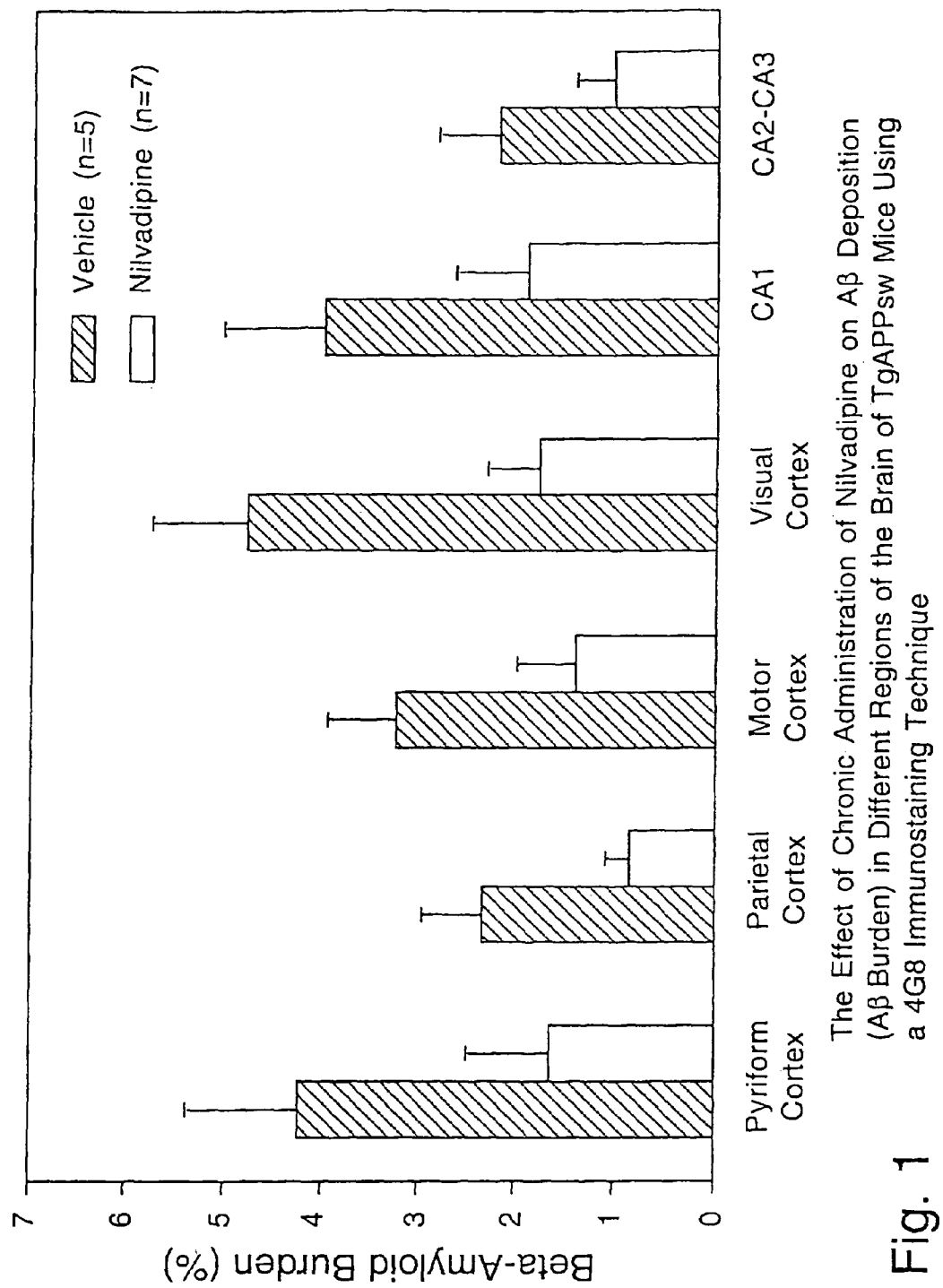
FIG. 1 is a bar graph that illustrates the effect of chronic administration of nilvadipine on Aβ deposition (Aβ burden) in different regions of the brain of TgAPP$_{sw}$ mice using a 4G8 immunostaining technique.

The present invention provides for the first time prophylactic methods for the inexorable progression of brain degeneration that is a hallmark of certain cerebral amyloidogenic diseases, such as, Alzheimer's disease (AD), in animals and humans, by administering nilvadipine (isopropyl-3-methyl-2-cyano-1,4-dihydro-6-methyl-4-(m-nitrophenyl)-3,5-pyridine-dicarboxylate; MW 385.4), a dihydropyridine analogue calcium channel antagonist.

In particular, one embodiment of the present invention provides a method for reducing β-amyloid deposition, β-amyloid neurotoxicity and microgliosis in animals or humans afflicted with a cerebral amyloidogenic disease or condition by administering therapeutically effective amounts of nilvadipine in unit dosage form. Because most cerebral amyloidogenic diseases, such as AD, are chronic, progressive, intractable brain dementias, it is contemplated that the duration of nilvadipine treatment will last for up to the lifetime of the animal or human. The cerebral amyloidogenic diseases or conditions include without limitation Alzheimer's disease, transmissible spongiform encephalopathy, scrapie, traumatic brain injury, cerebral amyloid angiopathy, and Gerstmann-Straussler-Scheinker syndrome.

In another embodiment of the present invention, a method is provided for reducing the risk of β-amyloid deposition, β-amyloid neurotoxicity and microgliosis in animals or humans suffering from traumatic brain injury (TBI) by administering to the animal or human a therapeutically effective amount of nilvadipine in unit dosage form immediately after the TBI and continuing the nilvadipine treatment for a prescribed period of time thereafter. It has been shown TBI increases the susceptibility to the development of AD, and thus it is believed, without being bound by the theory, that TBI accelerates brain Aβ accumulation and oxidative stress, which may work synergistically to promote the onset or drive the progression of AD.

The duration of nilvadipine treatment that is contemplated for those animals or humans suffering from a TBI can last for between about one hour to five years, preferably between about two weeks to three years, and most preferably between about six months and twelve months.

In a further embodiment of the present invention, a method is provided for diagnosing or determining the risk for developing a cerebral amyloidogenic diseases, such has AD, in an animal or human, by taking a first measurement of the plasma concentration of β-amyloid in the peripheral circulation of the animal or human; administering a therapeutically effective amount of nilvadipine in unit dosage form to the animal or human; taking a second measurement of the plasma concentration of β-amyloid in the peripheral circulation of the animal or human at a later time; and then calculating the difference between the first measurement and the second measurement. An increase in the plasma concentration of β-amyloid in the second measurement compared to the first measurement indicates a risk of developing or a possible diagnosis of a cerebral amyloidogenic disease in the animal or human. The duration of time that nilvadipine is administered between the first and the second plasma Aβ concentration measurements can last for between about one day to twelve months, preferably between about one week to six months, and most preferably between about two weeks to four weeks. It is contemplated that a small increase in plasma Aβ concentration after nilvadipine administration would be indicative of a risk of developing AD and/or diagnostic of the beginning stages of AD. Larger increases in plasma Aβ concentration after nilvadipine administration would reflect higher concentrations of Aβ liberated from the brain into the peripheral circulation and thus would be more indicative of a positive diagnosis of AD.

The therapeutically effective amount of nilvadipine that is administered in unit dosage form to animals or humans afflicted with a cerebral amyloidogenic disease or suffering from a traumatic brain injury, as well as administered for the purpose of determining the risk of developing and/or a diagnosis of a cerebral amyloidogenic disease in an animal or human, according to the methods of the present invention, can range from between about 0.05 mg to 20 mg per day, preferably from between about 2 mg to 15 mg per day, more preferably from between about 4 mg to 12 mg per day, and most preferably about 8 mg per day. The daily dosage can be administered in a single unit dose or divided into two, three or four unit doses per day.

In still another embodiment of the present invention is a method for pre-treating transplantable human or xenogenic neuronal stem cells by administering a therapeutically effective amount of nilvadipine to the neuronal stem cells prior to transplantation of the cells in the central nervous system of an animal or human that may be afflicted with a cerebral amyloidogenic disease, such as AD. Presumably, neuronal stem cells themselves would not have a significant deposition of Aβ. However, if the neuronal transplant is intended for an Aβ-burdened environment, pre-treatment of the neuronal stem cells should enhance the ability of the transplanted neurons to survive in their new environment by reducing the Aβ concentration and thus the Aβtoxicity therein. The therapeutically effective amount of nilvadipine that is administered in unit dosage form for pre-treating the neuronal stem cells can range from between about 1 nM to 3 µM, preferably between about 10 nM to 2 µM, and most preferably between about 100 nM to 1 µM. It is known that stem cells, when directed to differentiate into specific cell types, such as neuronal cells, offer the possibility of a renewable source of replacement cells and tissues to treat diseases and conditions, such Alzheimer's disease, Parkinson's disease or spinal cord injury. When such cells are transplanted/implanted into a patient, it is advisable not only to pre-treat the cells with nilvadipine but to begin therapeutic treatment of the patient with nilvadipine post-implantation as well.

It is contemplated that the methods of the present invention may be used on transgenic animal models for AD, such as the PDAPP and TgAPP$_{sw}$ mouse models, which may be eventually useful for treating, preventing and/or inhibiting conditions associated with amyloid deposition, β-amyloid neurotoxicity and microgliosis in the central nervous system of such animals or in humans. Thus, the present invention provides for transgenic animal models for AD which are constructed using standard methods known in the art and as set forth in U.S. Pat. Nos. 5,487,992; 5,464,764; 5,387,742; 5,360,735; 5,347,075; 5,298,422; 5,288,846; 5,221,778; 5,175,385; 5,175,384; 5,175,383; and 4,736,866.

Nilvadipine can be administered to a patient via various routes including parenterally, orally or intraperitoneally. Parenteral administration includes the following routes: intravenous; intramuscular; interstitial; intra-arterial; subcutaneous; intraocular; intracranial; intraventricular; intrasynovial; transepithelial, including transdermal, pulmonary via inhalation, ophthalmic, sublingual and buccal; topical, including ophthalmic, dermal, ocular, rectal, or nasal inhalation via insufflation or nebulization.

Nilvadipine that is orally administered can be enclosed in hard or soft shell gelatin capsules, or compressed into tablets. Nilvadipine also can be incorporated with an excipient and used in the form of ingestible tablets, buccal tablets, troches, capsules, sachets, lozenges, elixirs, suspensions, syrups, wafers, and the like. Further, nilvadipine can be in the form of a powder or granule, a solution or suspension in an aqueous liquid or non-aqueous liquid, or in an oil-in-water or water-in-oil emulsion.

The tablets, troches, pills, capsules and the like also can contain, for example, a binder, such as gum tragacanth, acacia, corn starch; gelating excipients, such as dicalcium phosphate; a disintegrating agent, such as corn starch, potato starch, alginic acid and the like; a lubricant, such as magnesium stearate; a sweetening agent, such as sucrose, lactose or saccharin; or a flavoring agent. When the dosage unit form is a capsule, it can contain, in addition to the materials described above, a liquid carrier. Various other materials can be present as coatings or to otherwise modify the physical form of the dosage unit. For example, tablets, pills, or capsules can be coated with shellac, sugar or both. A syrup or elixir can contain nilvadipine, sucrose as a sweetening agent, methyl and propylparabens as preservatives, a dye and flavoring. Additionally, nilvadipine can be incorporated into sustained-release preparations and formulations.

Nilvadipine can be administered to the CNS, parenterally or intraperitoneally. Solutions of nilvadipine as a free base or a pharmaceutically acceptable salt can be prepared in water mixed with a suitable surfactant, such as hydroxypropylcellulose. Dispersions also can be prepared in glycerol, liquid polyethylene glycols, and mixtures thereof, and in oils. Under ordinary conditions of storage and use, these preparations can contain a preservative and/or antioxidants to prevent the growth of microorganisms or chemical degeneration.

The methods of the present invention for reducing the pathological effects of Aβ in animals or humans suffering from diseases associated with amyloidosis, such as AD, will be described in more detail in the following non-limiting examples.

EXAMPLE 1

Chronic Administration of Nilvadipine on Aβ deposition (Amyloid Burden)

The effect of chronic administration of nilvadipine on Aβ deposition (amyloid burden) in different regions of the brain of TgAPP$_{sw}$ mice was examined using a 4G8 anti-Aβ monoclonal antibody immunostaining technique. The 4G8 immunostaining technique was chosen for determining the Aβ burden because of its robust signal and optimal results for quantitative analysis of Aβ deposition. Briefly, paraffin sections were subjected to immunohistochemistry as described previously (Nakagawa, Y et al., *Exp. Neurol.*, 163:244-252, 2000). Sections were deparaffinized in xylene, hydrated in a series of ethanol and deionized water, and subjected to an antigen retrieval step by immersing sections in 88% formic acid for 60 min before immunohistochemistry for Aβ. Sections were washed in water, and endogenous peroxidases were quenched using a freshly prepared mixture of methanol (150 ml) plus hydrogen peroxide (33%, 30 ml). The avidin-biotin complex method was used according to the instructions of the vendor (Vector Laboratories, Burlingame, Calif.). Amyloid burden was assessed by determining the percentage of the brain region that stained positive for Aβ. Negative controls included the application of the same immunohistochemistry protocol to sections, except preimmune serum was applied instead of primary antibody. TgAPP$_{sw}$ mice were divided into an experimental group that received an effective amount of nilvadipine (n=7) and a control group that received a vehicle (n=5).

As shown in FIG. 1, treatment with nilvadipine reduced the Aβ burden about 62% in the visual cortex compared to controls, about 65% in the parietal cortex compared to controls, about 58% in the motor cortex compared to controls, about 58% in the pyriform cortex compared to controls, about 52% in the CA1 region of the hippocampus compared to controls, and about 50% in the CA2-CA3 region of the hippocampus compared to controls.

EXAMPLE 2

Chronic Administration of Nilvadipine on Microglial Activation

The effect of chronic administration of nilvadipine on microglial activation in TgAPP$_{sw}$ mice was examined in three regions of the mouse brain using a CD45 immunostaining technique in which the number of CD45+microglia was determined.

Briefly, immunohistochemistry for CD45, a specific marker for leukocytes, was conducted on the cryostat brain sections. CD45-positive microglial cells were immunolocalized by incubation with a mouse monoclonal antibody against CD45 (Chemicon International) overnight at 4° C., followed by application of a biotinylated rabbit anti-mouse secondary antibody for 30 minutes. Detection of CD45 was completed with diaminobenzidine chromogen substrate, which produces a brown cell surface stain on CD45-positive microglial cells.

Figure 2:
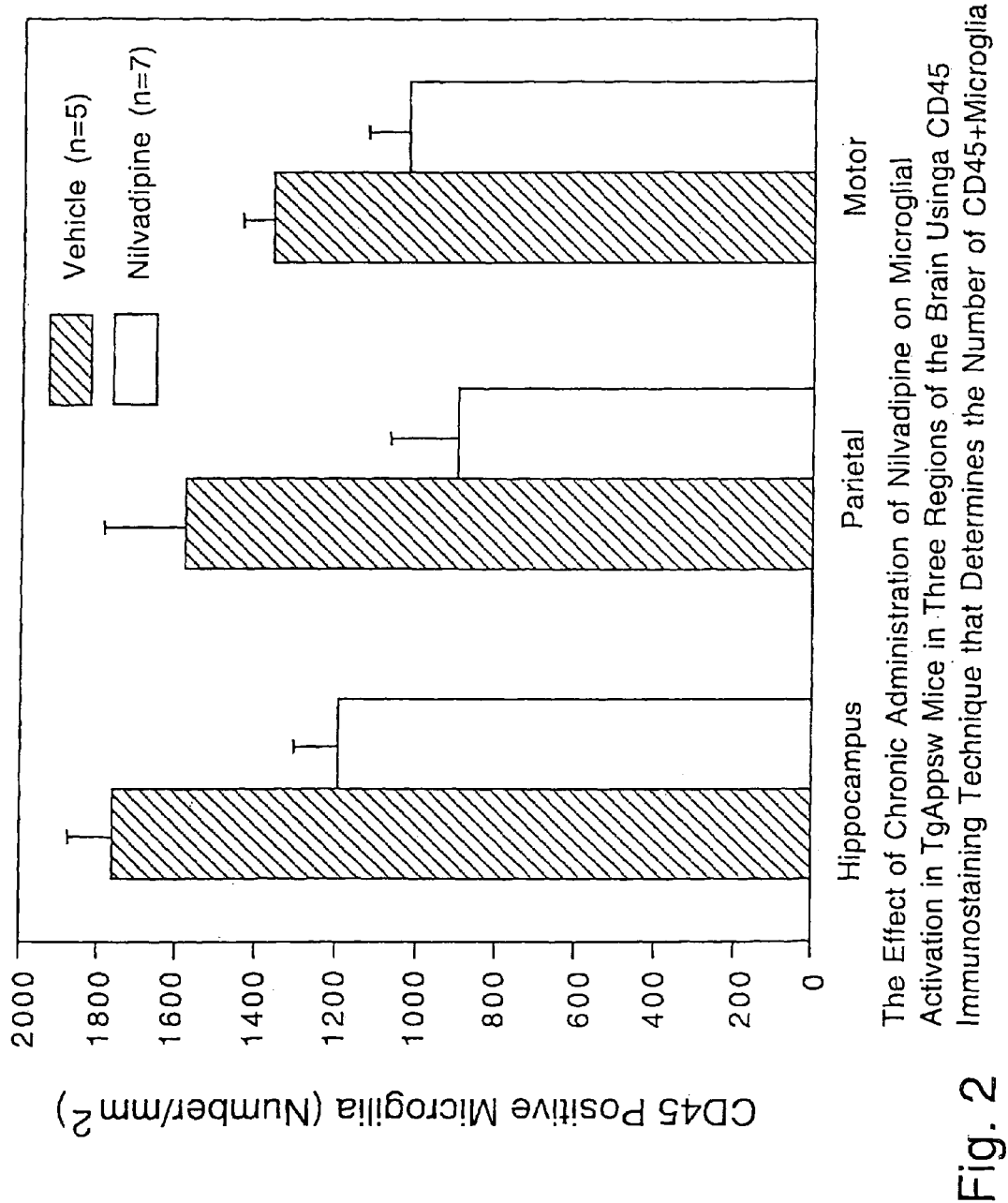
FIG. 2 is a bar graph that illustrates the effect of chronic administration of nilvadipine on microglial activation in TgAPP$_{sw}$ mice in three regions of the brain using a CD45 immunostaining technique that determines the number of CD45+microglia.

As shown in FIG. 2, nilvadipine treatment administered in an effective dosage amount reduced microglial activation about 33% in the hippocampus, about 43% in the parietal cortex, and about 27% in the motor cortex, when compared to controls.

EXAMPLE 3

The Effect of Nilvadipine Administration on Microglial Activation

Figure 3:
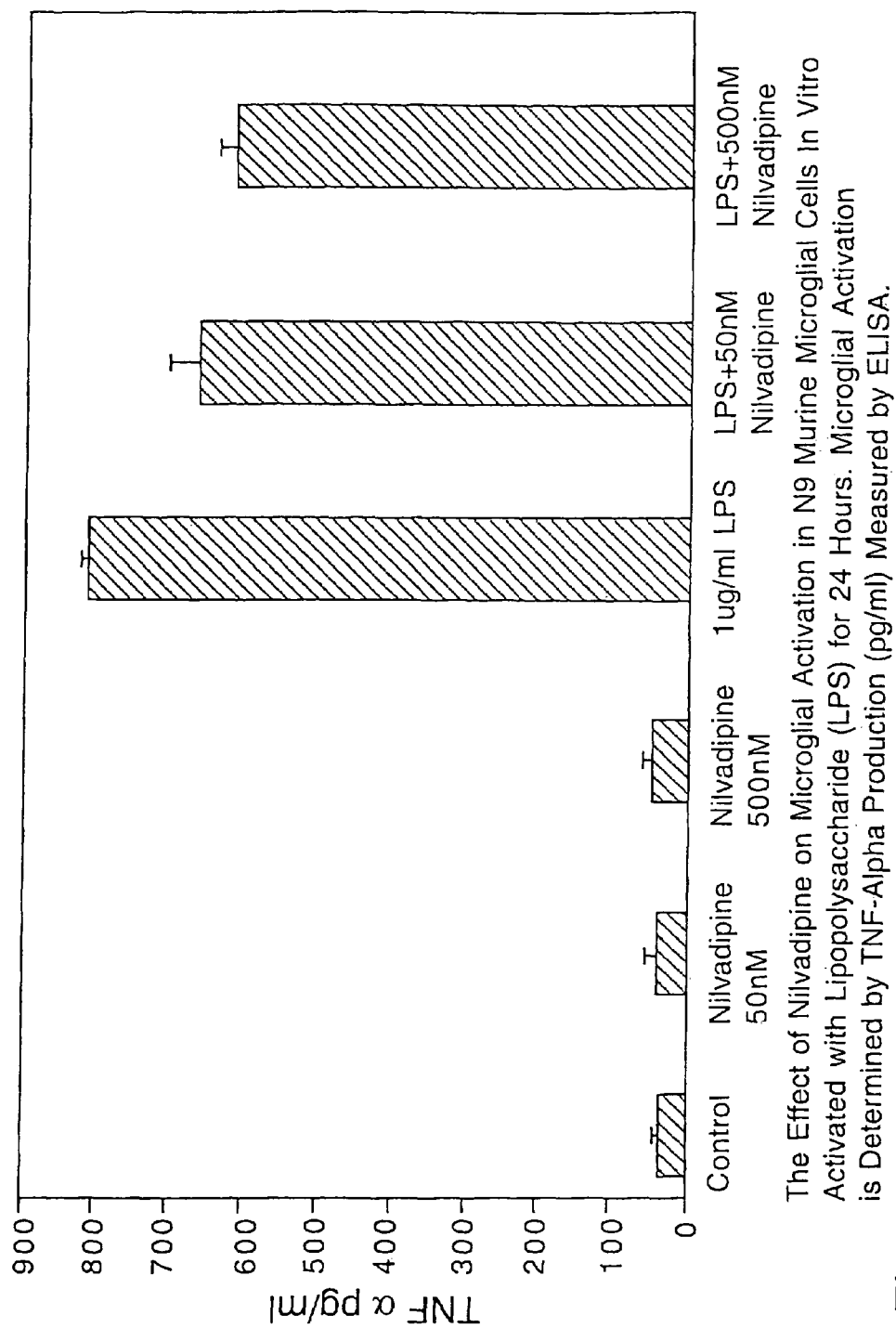
FIG. 3 is a bar graph that illustrates the effect of nilvadipine on microglial activation in N9 murine microglial cells in vitro activated with lipopolysaccharide (LPS) for 24 hours. Microglial activation is determined by TNF-α production (pg/ml) measured by ELISA.

The effect of nilvadipine on microglial activation was examined in N9 murine microglial cells in vitro activated with lipopolysaccharide (LPS) for 24 hours. N9 murine micoglial cells are well characterized scavenger murine microglial clones derived from embryonic mouse brain. The extent of microglial activation was determined by TNF-α production (pg/ml) measured by ELISA. As shown in FIG. 3, microglial cells not activated with LPS (control cells) produced about 40 pg/ml TNF-α. Microglial cells in the presence of 50 nM nilvadipine produced about 40 pg/ml TNF-α. Increasing nilvadipine administration 10-fold (500 nM) did not change TNF-α production. Microglial cells in the presence of 1 μg/ml LPS produced about 820 pg/ml TNF-α, an increase of about 95% from the control cells and nilvadipine-administered cells. Microglial cells in the presence of both 1 μg/ml LPS plus 50 nM nilvadipine produced about 670 pg/ml TNF-α. LPS plus 500 nM nilvadipine administration decreased TNF-α production to about 610 pg/ml. Thus, nilvadipine opposed the LPS-induced microglial activation by about 20 to 25%.

EXAMPLE 4

The Effect of Nilvadipine Administration on Aβ Neurotoxicity

The effect of nilvadipine administration (10 nM and 100 nM) on Aβ neurotoxicity was examined using human neuronal progenitor cells (HNPC) treated for three days with 30 μM of pre-aggregated Aβ1-40 (AgA). HNPC cells differentiate into neurons readily upon treatment with cyclic AMP. Cyclic AMP (1 mM) (Sigma) was added to the culture medium and the HNPC cells were incubated at 37° C. for 48 hours or more under serum free conditions. This medium allowed differentiation of the progenitors into cells of neuronal lineage, as was confirmed by the staining of most of the cells with antibodies against the microtubule-associated protein, MAP-2. Neurotoxicity was assessed by measuring the amount of lactic dehydrogenase (LDH; an intracellular enzyme found in all cells) released from the cells.

Figure 4:
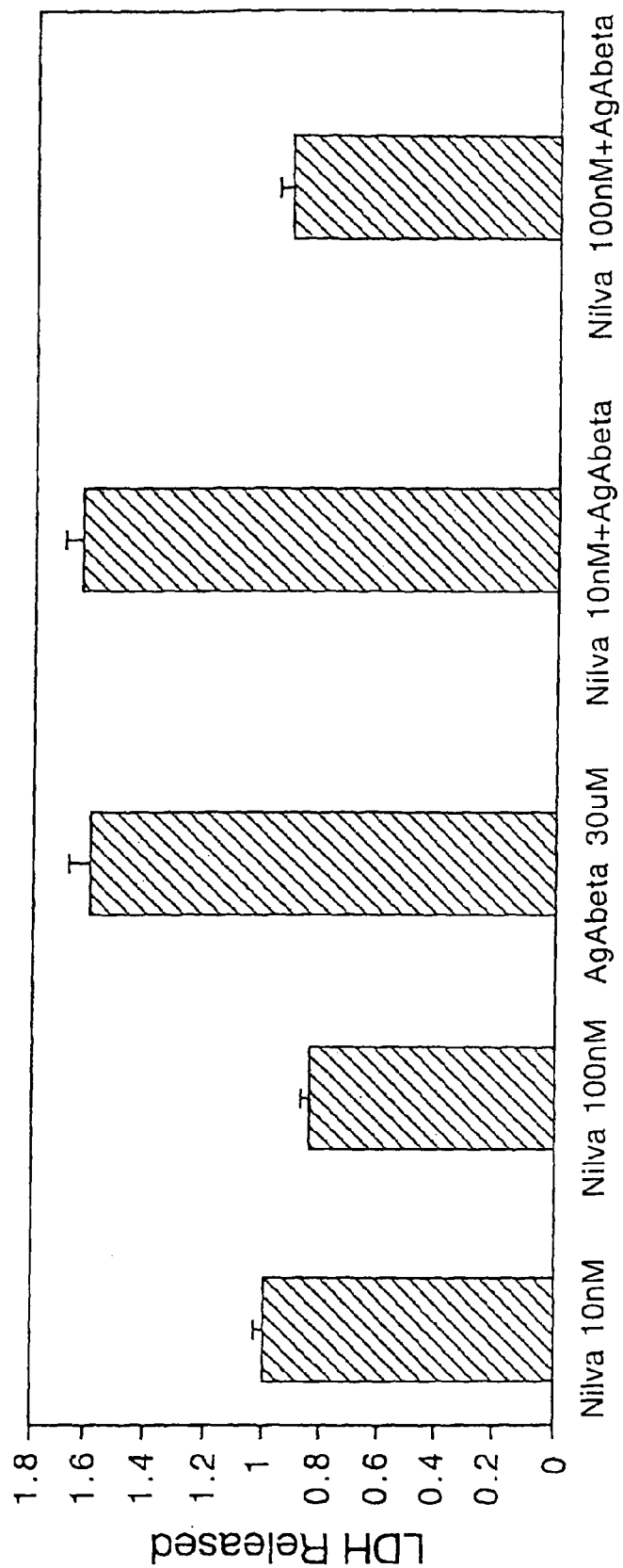
FIG. 4 is a bar graph that illustrates the effect of nilvadipine administration on Aβ neurotoxicity using HPNC cells treated for three days with 30 µM of pre-aggregated Aβ1-40 (AgAβ). Neurotoxicity is assessed by measuring the amount of lactic dehydrogenase (LDH) released from cells.

As shown in FIG. 4, treatment of the cells with AgAβ produced about a 44% increase in LDH release compared to treatment of the cells with nilvadipine. There was no change in LDH release when 10 nM nilvadipine was added along with AgAβ. However, when the dosage amount of nilvadipine was increased 10-fold to 100 nM, the amount of LDH release was decreased by about 44%.

EXAMPLE 5

The Effect of Nilvadipine Administration on APP Processing

The effect of nilvadipine on APP processing was examined using human glioblastoma cells transfected with $APP_{sw}$. The cells were treated with 50 nM and 250 nM nilvadipine for 24 and 48 hours, and production of Aβ1-40 in the culture medium was measured by using a commercially available human Aβ1-40 ELISA (Biosource, CA).

Figure 5A:
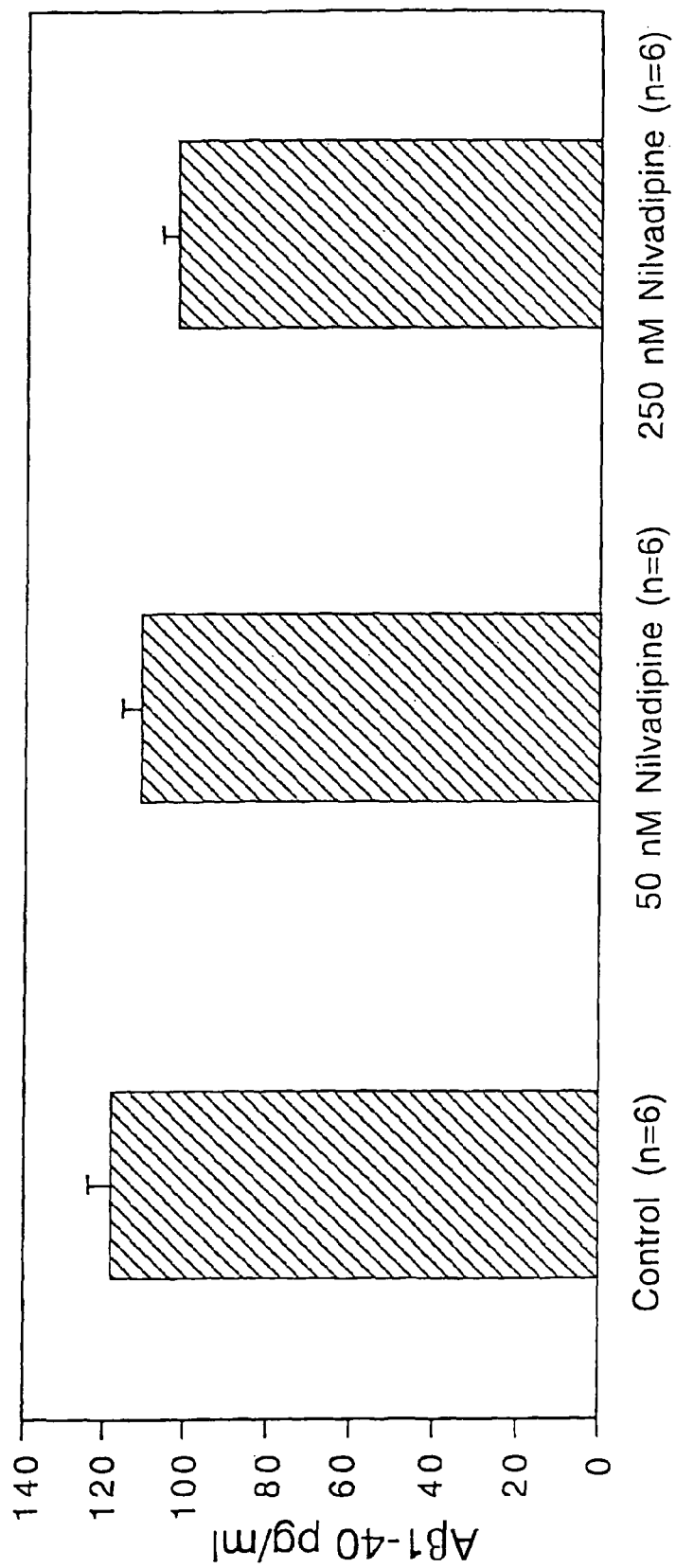
FIG. 5 is a bar graph that illustrates the effect of nilvadipine on APP processing using human glioblastoma cells transfected with APP$_{sw}$. Cells were treated with 50 nM and 250 nM nilvadipine for 24 hours (FIG. 5A) and for 48 hours (FIG. 5B). Production of Aβ1-40 in the culture medium was measured by ELISA.
Figure 5B:
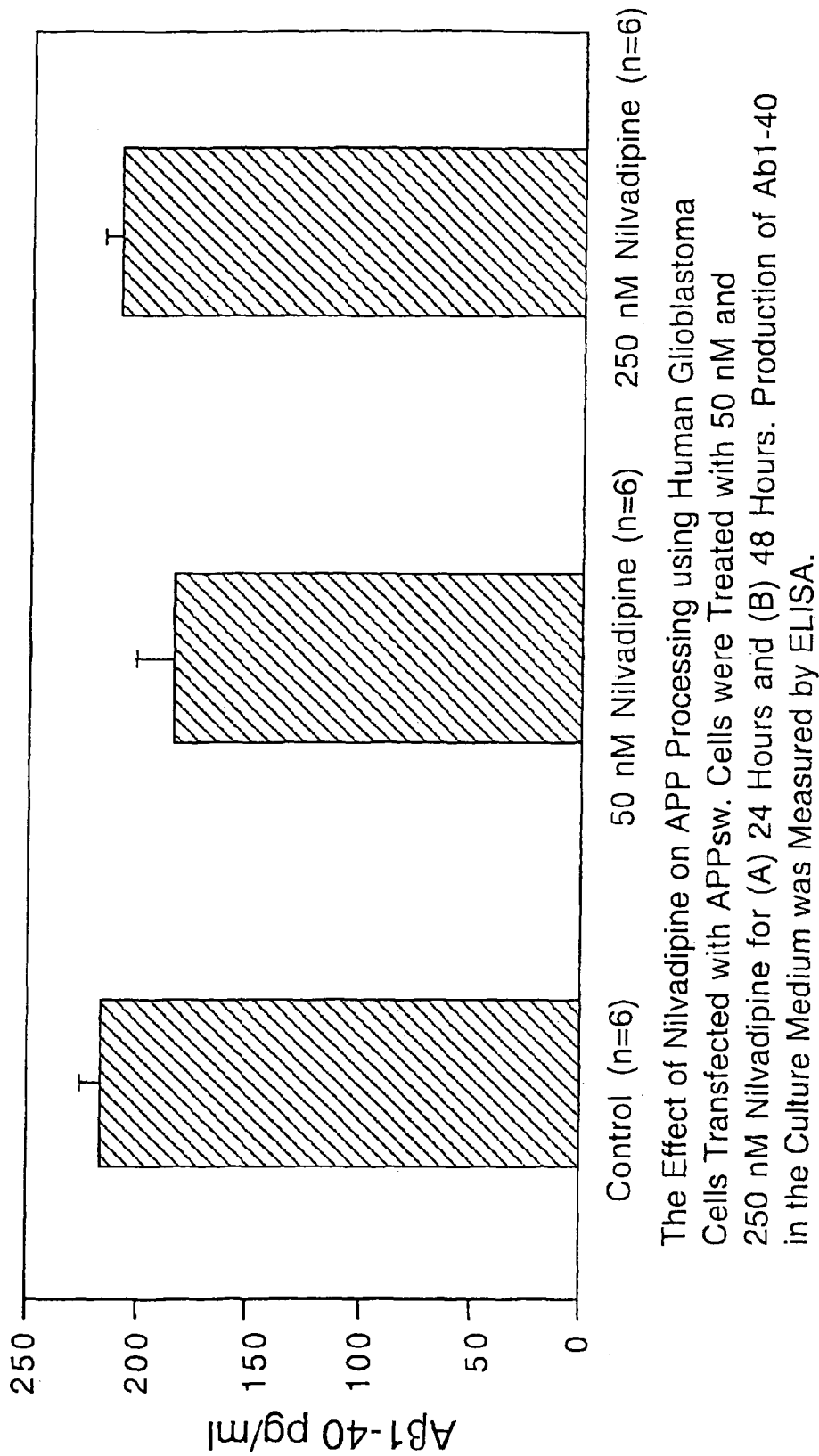

As shown in FIG. 5A, after 24 hours of treatment, 50 nM of nilvadipine reduced the production of Aβ1-40 by about 9%, and 250 nM of nilvadipine reduced Aβ1-40 production by about 15%. After 48 hours of treatment (FIG. 5B), 50 nM of nilvadipine reduced the production of Aβ1-40 by about 18%, and 250 nM of nilvadipine reduced Aβ1-40 production by about 5%.

EXAMPLE 6

Effect of Nilvadipine Administration on Plasma Aβ Levels

The effect of nilvadipine administration on plasma Aβ levels (pg/ml) was examined using 2 year old $TgPS/APP_{sw}$ mice. Animals were treated intraperitoneally (I.P.) every day for three and one half weeks with nilvadipine (1.5 mg/kg of body weight; n=10) or vehicle only (50% DMSO in PBS; n=12). Following this treatment, 100 μl of blood were collected from the tail vein of the animals using EDTA (4%) as an anticoagulant. Blood samples were centrifuged at 4000 g for 1 min and the plasma was collected and diluted four times before being assayed for human Aβ1-40 using a commercially available human Aβ1-40 ELISA (Biosource, CA).

Figure 6:
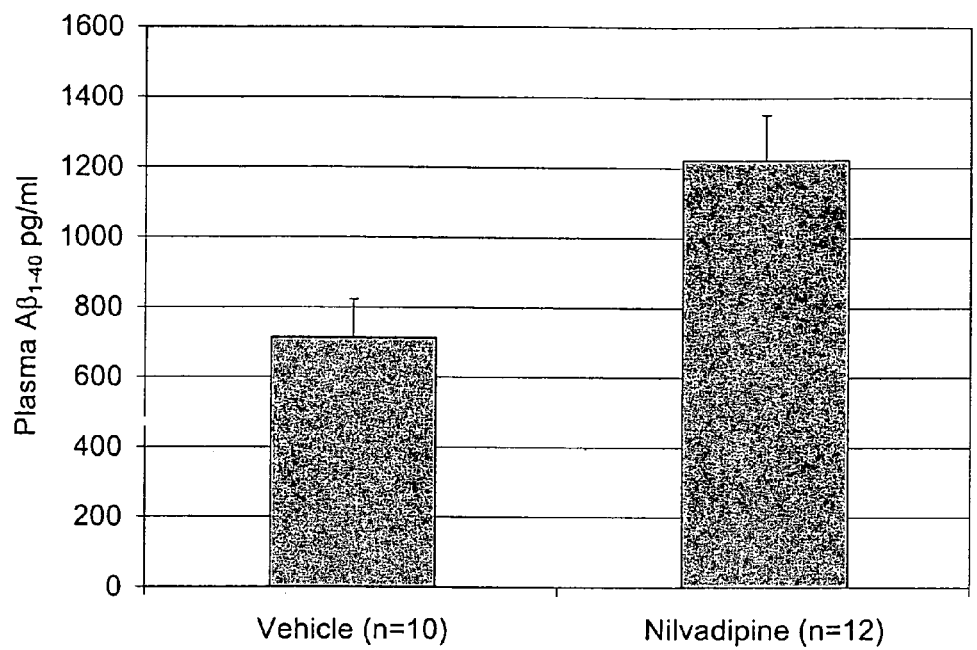
FIG. 6 is a bar graph that illustrates the effect of nilvadipine on plasma Aβ levels in two-year old TgPS/APP$_{sw}$ mice. Animals were treated intraperitoneally every day for three and a half weeks with nilvadipine (1.5 mg/kg of body weight).

As shown in FIG. 6, I.P. administration of nilvadipine to $TgPS/APP_{sw}$ mice at a dose of 1.5 mg/kg body weight for three and one half weeks resulted in a 42% increase in the plasma levels of Aβ (pg/ml) compared to the control animals.

General Conclusions

Chronic administration of nilvadipine significantly reduced the amount of AP present in different regions of the cerebral cortex and hippocampus of transgenic mice, as well as significantly reducing the degree of microglial activation. When N9 murine microglial cells were activated with LPS, nilvadipine administration significantly reduced LPS-induced microglial activation. Furthermore, nilvadipine effectively opposed the neurotoxic effect of AgAβ on a human precursor neuronal cell line. Although the production of Aβ1-40 was not significantly decreased by nilvadipine treatment, there was a trend toward decreased Aβ1-40 production after nilvadipine administration. This reduction in Aβ1-40 potentially reflects reduced production, but other mechanisms to which the lowered appearance of Aβ1-40 might be attributable would include, without limitation, phagocytosis or other destruction, or cellular effects which prevent its aggregation and detection. Regardless of the mechanism, however, the data suggest that the presence of nilvadipine concomitantly reduced the presence of Aβ1-40. Finally, chronic administration of nilvadipine I.P. to 2-year old $TgPS/APP_{sw}$ mice significantly increased the plasma levels of Aβ, suggesting that, in addition to the ability of nilvadipine to reduce deposition of Aβ in the brain, nilvadipine treatment may reduce Aβ that already is already deposited in the brains of afflicted subjects.

In view of the above data, it can be extrapolated that nilvadipine administration to animals or humans afflicted with a cerebral amyloidogenic disease, such as AD, can significantly decrease the amount of Aβ deposition in critical regions of the brain that characteristically demonstrate an abundance of such pathological deposits as well as reduce the amount of Aβ already deposited in the brain. Additionally, nilvadipine administration may oppose the neurotoxic effects of Aβ, effects which are believed to be responsible for the widespread and devastating neuronal destruction seen with AD, as well as reduce microglial activation that causes the characteristic inflammatory response seen in the brains of AD patients. Finally, nilvadipine treatment may reduce the concentration of already deposited Aβ in brains of animals or humans afflicted with cerebral amyloidogenic diseases such as AD.

It will be apparent to those skilled in the art that various modifications and variations can be made in the methods of the present invention without departing from the spirit or scope of the invention. Thus, it is intended that the present invention include modifications and variations that are within the scope of the appended claims and their equivalents.

The invention claimed is:

1. A method for reducing β-amyloid deposition, β-amyloid neurotoxicity and microgliosis in animals and humans afflicted with Alzheimer's disease, consisting essentially of the administration of nilvadipine to the animal or human.

2. The method of claim 1, wherein the amount of nilvadipine administered is between about 0.05-20 mg per day.

3. The method of claim 1, wherein the amount of nilvadipine administered is between about 2-15 mg per day.

4. The method of claim 1, wherein the amount of nilvadipine administered is between about 4-12 mg per day.

5. The method of claim 1, wherein the amount of nilvadipine administered is 8 mg per day.

6. The method of claim 1, wherein the duration of nilvadipine treatment lasts for up to the lifetime of the animal or human.

7. The method of claim 1, wherein the administration of nilvadipine to the animal or human is via parenteral, oral or intraperitoneal administration.

8. The method of claim 7, wherein the administration is oral administration that is in the form of hard or soft shell gelatin capsules, tablets, troches, sachets, lozenges, elixirs, suspensions, syrups, wafers, powders, granules, solutions or emulsions.

9. The method of claim 7, wherein the administration is oral administration that is in the form of a sustained release formulation.

10. A method for reducing β-amyloid deposition, β-amyloid neurotoxicity and microgliosis in animals or humans afflicted with Alzheimer's disease consisting essentially of administering to the animal or human a pharmaceutical composition consisting of a therapeutically effective amount of nilvadipine and a pharmaceutically acceptable carrier.

11. The method of claim 1, wherein said administration is chronic administration.

12. The method of claim 1, wherein said method is for use in humans.

* * * * *